(12) United States Patent
Scott et al.

(10) Patent No.: US 9,939,233 B2
(45) Date of Patent: Apr. 10, 2018

(54) LASER BEAM PATTERN PROJECTOR

(71) Applicant: Doubleshot, Inc., Rohnert Park, CA (US)

(72) Inventors: Miles L. Scott, Rohnert Park, CA (US); Alan Shulman, Santa Rosa, CA (US)

(73) Assignee: DOUBLESHOT, INC., Santa Clara, CA (US)

( * ) Notice: Subject to any disclaimer, the term of this patent is extended or adjusted under 35 U.S.C. 154(b) by 789 days.

(21) Appl. No.: 14/195,498

(22) Filed: Mar. 3, 2014

(65) Prior Publication Data

US 2014/0176954 A1    Jun. 26, 2014

Related U.S. Application Data

(63) Continuation-in-part of application No. 12/243,829, filed on Oct. 1, 2008, now Pat. No. 8,662,707.

(60) Provisional application No. 60/976,796, filed on Oct. 2, 2007.

(51) Int. Cl.

| | |
|---|---|
| *F41H 13/00* | (2006.01) |
| *G01N 21/55* | (2014.01) |
| *F41H 3/00* | (2006.01) |
| *F41H 11/02* | (2006.01) |
| *G01S 17/88* | (2006.01) |
| *F41G 3/14* | (2006.01) |

(52) U.S. Cl.
CPC .......... *F41H 13/0056* (2013.01); *F41G 3/14* (2013.01); *F41H 3/00* (2013.01); *F41H 11/02* (2013.01); *F41H 13/005* (2013.01); *G01N 21/55* (2013.01); *G01S 17/88* (2013.01)

(58) Field of Classification Search
CPC .......... F41G 1/35; F41G 1/38; F41H 13/0056; F41A 33/00
USPC .......................................................... 356/5.1
See application file for complete search history.

(56) References Cited

U.S. PATENT DOCUMENTS

| | | | | |
|---|---|---|---|---|
| 7,256,899 | B1 * | 8/2007 | Faul ................... | G01B 11/2522 345/420 |
| 2004/0263932 | A1 * | 12/2004 | Sakai ................... | H04N 9/3129 359/196.1 |
| 2006/0234191 | A1 * | 10/2006 | Ludman ................... | F41G 1/35 434/11 |
| 2007/0274353 | A1 * | 11/2007 | Hauck ................. | F41H 13/0056 372/9 |

* cited by examiner

*Primary Examiner* — Luke D Ratcliffe
(74) *Attorney, Agent, or Firm* — Finnegan, Henderson, Farabow, Garrett & Dunner LLP

(57) ABSTRACT

Methods and systems consistent with some embodiments presented provide methods for denying visual access to a first area from a target area. In some embodiments, methods for denying visual access from a target area may include generating a structured light pattern and projecting the structured light pattern from onto the target area. Reflections and retroreflections from the target area can indicate the presence of sensors. Characterization of one or more sensors in the target area based on the reflections and retroreflections can be performed. Parameters of the structured light pattern, such as color content, amplitude, pattern, and movement of the pattern, can be adjusted based on the type of sensor detected.

7 Claims, 8 Drawing Sheets

200
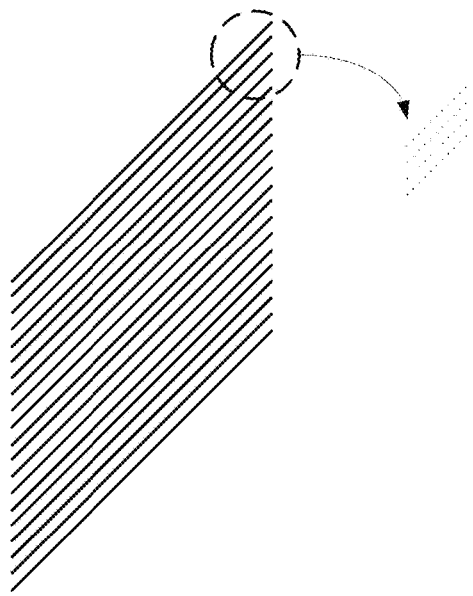
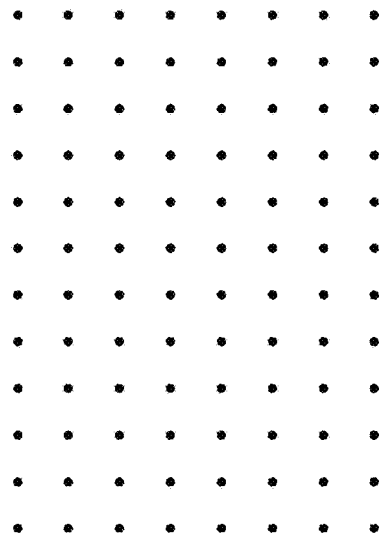
FIG. 2A
FIG. 2B
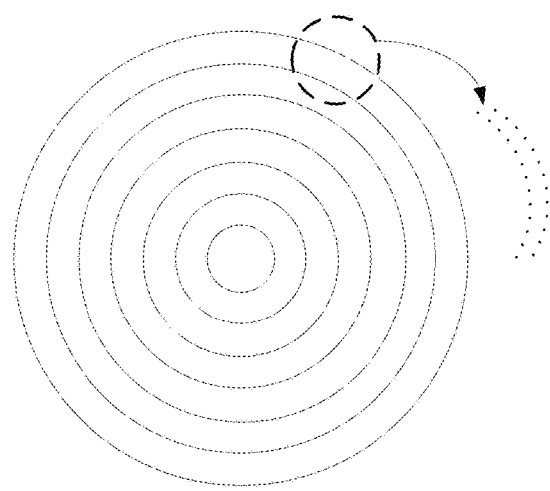
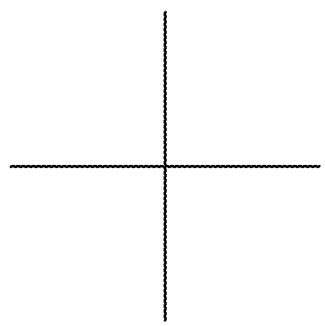
FIG. 2C
FIG. 2D

LASER BEAM PATTERN PROJECTOR

CROSS-REFERENCE TO RELATED APPLICATIONS

This application is a continuation-in-part of U.S. patent application Ser. No. 12/243,829, filed Oct. 1, 2008, which claims the benefit of priority of U.S. Provisional Application No. 60/976,796, filed Oct. 2, 2007, entitled "Laser Beam Pattern Projector," the disclosure of which is expressly incorporated herein by reference in its entirety.

BACKGROUND

Technical Field

Embodiments consistent with the presently-claimed invention are related to laser projection systems and, in particular, to methods and systems for creating an area of denied visual access. Embodiments are further related to characterizing sensors detected by reflection and retroreflection of the projected laser pattern.

Discussion of Related Art

Non-lethal directed energy systems are increasingly used by law enforcement because of their ability to reduce fatalities and collateral damage. Some directed weapon systems use electromagnetic energy, such as lasers, to visually impair identified visual systems temporarily or to warn of suspected threats prior to using other protective measures. Other directed energy systems may be used proactively to protect a person or an object from unknown targets that may be in the surrounding area. For example, local authorities may wish to secure an area in preparation for a public appearance by a government official or a moving vehicle.

In certain situations, however, existing directed energy systems utilizing lasers may be of limited effectiveness. For example, existing system may be ineffective when applied to large geographic areas. Existing systems have to blanket a large area with a more or less uniform illumination or scan the area with a single spot or line. The first case requires a very high power source; while the second approach is limited by the time required to scan a large area with a single spot or line. The scan time may limit dwell time and may require impractical rates of motion for large areas or multiple systems. In another example, some existing systems are designed to cause temporary vision impairment over a narrow range within a target area at some distance from the object or person to be protected. Often, these systems are aimed by an operator at a single location or manually swept across a target area. As a result, the ability to neutralize an undisclosed threat in a broad area is limited by the operator. Further, sufficient dwell time may not be available to cause the desired effects of aversion or disruption. Some existing systems have difficulty denying visual access across target areas having varying geographic and structural conditions. Some systems, for example, may be safely operated when targets are at an extended distance or widely dispersed. These systems, however, may create eye safety concerns when used at closer distances, such as in narrow corridors or within a building.

SUMMARY

Provided herein is a method for denying visual access from a target area, the method comprising by generating a structured light pattern, projecting the structured light pattern onto the target area, receiving reflected and retroreflected light returning from the target area, detecting the presence of a sensor in the target area, and analyzing the reflected and retroreflected light to characterize the sensor.

There is also provided a system that includes: a light source and a diffractive optic element configured to project a structured light pattern onto a target area; a detection device for receiving reflected and retroreflected light returning from the target area and generating data corresponding to the reflected and retroreflected light; and a controller configured to receive the data, analyze the data to determine the presence of a sensor in the target area, and further analyze the data to characterize the sensor.

It is to be understood that both the foregoing general description and the following detailed description are exemplary and explanatory only and are not restrictive of the invention. Further embodiments and aspects of the presently-claimed invention are described with reference to the accompanying drawings, which are incorporated in and constitute a part of this specification.

BRIEF DESCRIPTION OF THE DRAWINGS

FIGS. 2A, 2B, 2C, and 2D show exemplary images generated by transmitting a light source through a diffractive optic element in a manner ???.

DETAILED DESCRIPTION

Reference will now be made in detail to embodiments, examples of which are illustrated in the accompanying drawings. Wherever possible, the same reference numbers will be used throughout the drawings to refer to the same or like parts.

Figure 1:
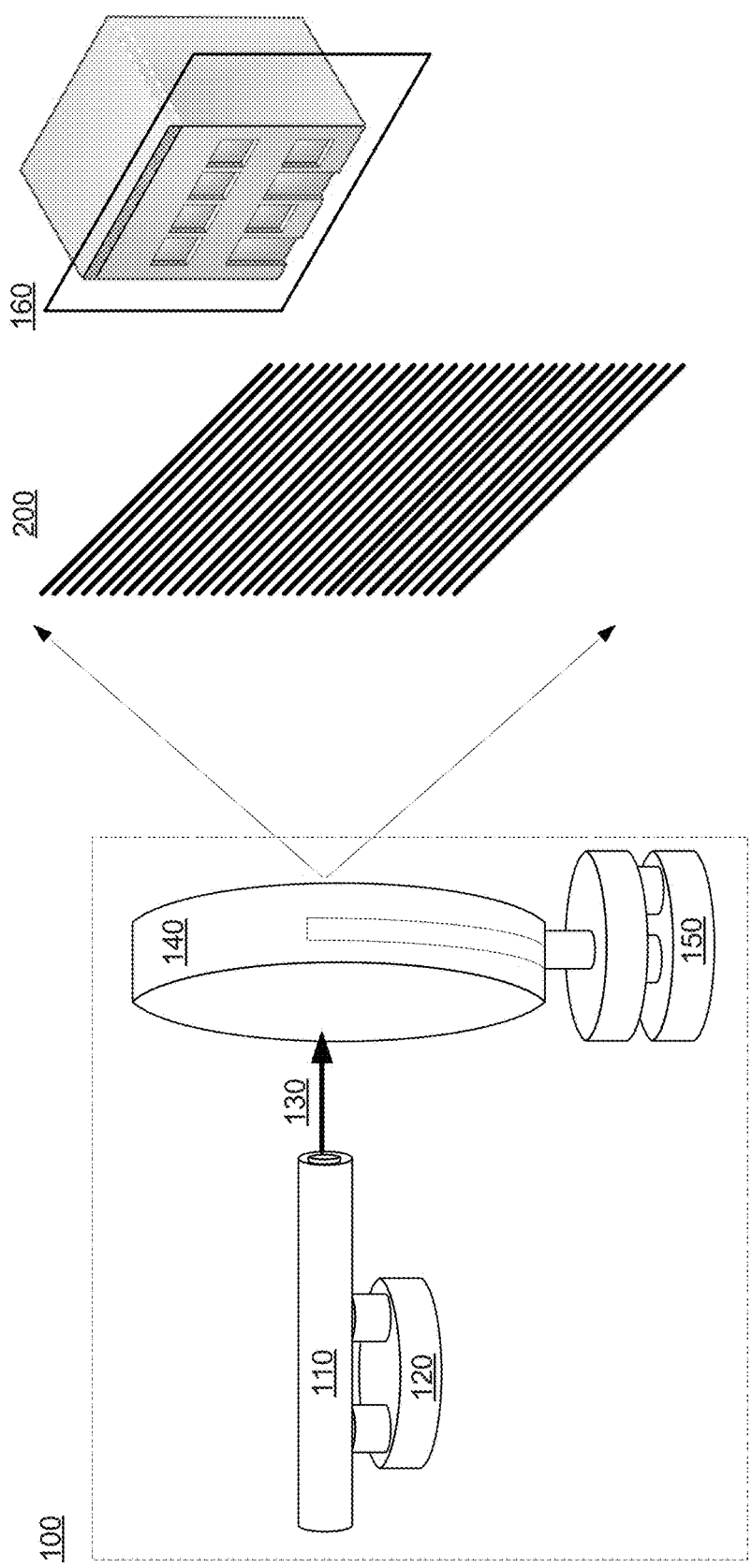
FIG. 1 shows a block diagram illustrating an exemplary system for creating an area of denied visual access.

FIG. 1 shows a block diagram illustrating components in system 100 for creating an area of denied visual access. As shown in FIG. 1, system 100 comprises a light source 110 and a diffractive optic element 140. Light source 110 may be, for example, a laser or a partially coherent light source. Lasers may be, for example, a laser diode, a solid state laser, or a gas laser. In certain embodiments, light source 110 may be a green diode-pumped solid state (DPSS) laser. DPSS lasers may operate in continuous wave (CW), quasi-CW, analog modulated, or pulsed mode. The laser wavelength may be chosen based on the application, with exemplars of near UV or visible for biological visual systems (for example, human eyes), and the full range of optical wavelengths for electronic visual systems. Alternatively, light source 110 may be a partially coherent light source, such as a light emitting diode (LED).

Diffractive optic element 140 may be a passive optical element having a surface consisting of complex microstructures forming a surface relief profile. In some embodiments, diffractive optic element 140 may be formed from a polymer substrate, such as polyimide or typical optical materials such as fused silica, germanium, or glass. The diffractive optic element 140 may be configured as a transmissive or reflective element. The surface relief profile may be created using various techniques including, but not limited to, lithography, direct machining, and replication. In some cases, a particular fabrication technique may be used based on the geometry and complexity of the microstructures required to produce a particular relief pattern. For example, lithographic techniques similar to those used in semiconductor manufacturing may be used to create very complex multiple-layer microstructures. In some embodiments, the surface relief profile may be generated by a computer program executed by a processor. The computer program, for example, may execute instructions to create a particular surface relief profile corresponding to a desired structured light pattern. The computer program may be adapted for use with a variety of fabrication techniques, including those previously discussed. Diffractive optic element 140 may be comprised of multiple components lenses, diffraction gratings and other optics, which together act as a diffractive optic system, even though referred to herein as an "element." In some embodiments, a non-diffractive optic element (not shown) may be used in combination with diffractive optic element 140 to produce a desired structured light pattern. For example, a non-diffractive optic element, such as a Fresnel optic element, a traditional ground optic element, or a cast optic element, may be used to create a line in response to receiving an optical signal. Diffractive optical element 140 may be coupled to receive the resulting line output from the non-diffractive optic element to repeat the line, or other projected pattern elements, forming a structured pattern.

Diffractive optic element 140 may be an active optical element. This element may be a liquid crystal spatial light modulator, DLP™, or Liquid Crystal on Silicon (LCOS) micro-display panel configured as a spatial light modulator. An active optical element may be driven by a computer, an electronics board, or play back of pre-calculated data series. In response to receiving the data series, the active optic element may create structured light patterns that varies based on the received data series. For example, in some cases, using an active the process of using an active optical element to create a structured light pattern may be similar to the process used to send electronic data to a desk top projector. The difference, however, being that the pattern on the micro-display panel is a diffractive pattern where pixels have a phase shift component or a phase shift component and a gray scale value. The active diffractive optic element 140 may be either reflective or transmissive.

In certain embodiments, light source 110 may be mounted on optional positioning unit 120 with diffractive optic element 140 mounted to the light source 110 so that both devices move together. Positioning unit 120 and optical mount 150 enable light source 110 and diffractive optic element 140 to be moved and repositioned along multiple axes.

In certain embodiments, light source 110 may be mounted on an optional positioning unit 120. Similarly, diffractive optic element 140 may be mounted on an optical mount 150. Positioning unit 120 and optical mount 150 allow light source 110 and diffractive optic element 140 to be moved and repositioned along multiple axes. Positioning unit 120 and/or optical mount 150 may be, for example, one or a combination of, actuators, optical mounts, gimbals, or similar devices. For example, in some embodiments, positioning unit 120 or optical mount 150 may be a positioning system consisting of multiple piezoelectric actuators. The range of motion, in this case, may be based on the number of piezoelectric actuators or other electromechanical factors. For example, by using six piezoelectric actuators, positioning unit 120 and/or optical mount 150 can move in six independent axes. The operation of positioning unit 120 and optical mount 150 may be controlled by one or a combination of software, firmware or hardware. Operating parameters may include, but are not limited to, speed of adjustment, resolution of movement, and pivot point. In some embodiments, positioning unit 120 and/or optical mount 150 may be a gimbal with some small degree of freedom of motion. Using a gimbal may allow the light source 110 and/or diffractive optic element 140 to move in a random pattern determined by external forces such as the motion of a vehicle upon which system 100 may be mounted.

Light source 110 projects an optical signal 130 toward diffractive optic element 140. Diffractive optic element 140 receives optical signal 130 from light source 110, and transforms optical signal 130 into a structured light pattern, illustrated by image 200. FIGS. 2A, 2B, 2C, and 2D show exemplary structured light patterns that may be generated. As shown in FIG. 2A, image 200 may be comprised of a series of lines. The spacing of the line may be changed depending on various factors, such as the surface relief profile of diffractive optic element 140. The lines may be parallel or arranged in some other fashion. Similarly, as shown in FIG. 2C, image 200 may be one or more circles. The circles may be concentric, overlapping, or otherwise arranged. The circles may comprise closely spaced dots or lines. Other exemplary patterns for image 200 are a dot-array as shown in FIG. 2B or a cross as shown in FIG. 2D, although other patterns are also possible.

Returning now to FIG. 1, image 200 is projected onto target area 160. Target area 160 is the area potentially containing a threat whose vision the system seeks to block. In certain embodiments, image 200 is moved around in target area 160 to create a moving pattern, as optical mount 120 redirects the light source 110, and thus optical signal 130 in a different direction. Image 200, in some cases, may also be projected in a stationary manner for some periods of time. By moving image 200 around in target area 160, an area of denied visual access may be created. Moving image 200 may create an aversion response when image 200 is viewed by a human or disable the use of an electronic visual system.

In certain embodiments, a green DPSS laser may be used as light source 110. It is known that the human eye has a heightened sensitivity to green light. As a result, the aversion response caused by viewing image 200 when it is created using a green laser may be enhanced.

In some embodiments, light source 110 may be a DPSS laser operating in quasi-CW, amplitude modulated, analog or pulsed amplitude modulated, or wavelength modulated. In these cases, it may be necessary to coordinate the pulse rate of the laser with the movement of the structured light pattern that is image 200. Further the modulation of the light source may be chosen to create effects in visual systems.

In some embodiments, light source 110 may have a variable output power, such that the light source may be made brighter or dimmer, manually or automatically. For example, light source 110 may be made brighter or stronger if system 100 is farther away from target area 160, or dimmer if system 100 is closer. Alternatively or additionally, system 100 may be adjusted to produce a stronger light to increase the protection of the field of denied visual access or to frustrate countermeasures that may try to block the light. In some embodiments, light source 110 may be adjusted automatically in response to conditions perceived by system 100. For example, system 100 may comprise a detector that detects the level of ambient light, or whether it is night or day, or whether there is precipitation, or the amount of optical signal 130 return energy. The detector may provide information to system 100 to adjust the system selectable output power. System 100 may also be configured based on the structural and geographic features of target area 160. For example, higher output power may be required based on the distance between system 100 and target area 160. In some embodiments, the distance may be determined using a remote distance measuring device, such as a laser radar, a map, a global positioning system, or other similar device or technique.

Consistent with some embodiments, light source 110 may be a partially-coherent light source, such as a light emitting diode. Partially-coherent light sources may produce a more distributed energy spectrum compared to energy emanating from a coherent light source. Accordingly, the resulting structured light pattern may be less defined. Partially-coherent light sources may also require more power to project image 200 on to target area 160 at a given distance as compared to using a coherent light source.

Figure 3:
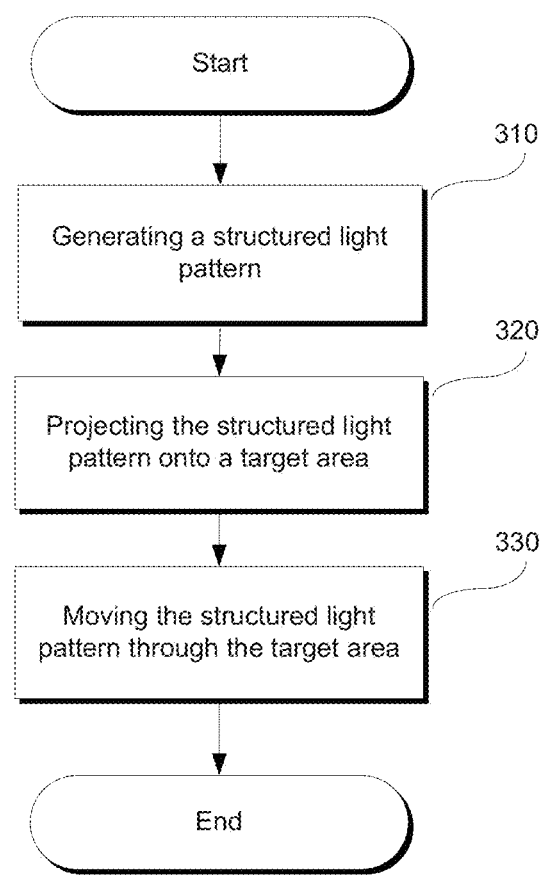
FIG. 3 shows a flowchart illustrating steps in an exemplary method for creating an area of denied visual access.

FIG. 3 shows a flowchart illustrating steps in an exemplary method for creating an area of denied visual access. It will be readily appreciated by one having ordinary skill in the art that the illustrated procedure can be altered to delete steps, move steps, or further include additional steps.

In step 310, an image is generated by projecting an optical signal through the diffractive optic element. An optical signal is emitted by, for example, light source 110 (as shown in FIG. 1) in the direction of a diffractive optic element, such as diffractive optic element 140 (also shown in FIG. 1). The passing of the optical signal through a diffractive optic element creates a structured light pattern, or image. The structured light pattern may have various dimensions and qualities depending, at least in part, on the surface relief profile or refractive index of the optic element or the incident angle between the optical signal and the diffractive optic element.

In some embodiments, a user may select one of a plurality of diffractive optic elements, each producing a distinct structured light pattern. For example, in a system comprising multiple diffractive optic elements, a user may select, using a computer controlled or mechanical interface, one of a plurality of diffractive optic elements. In a similar manner, a user may select one of a plurality of light sources to use in combination with one of a plurality of diffractive optic elements. In some embodiments, the selected combination of diffractive optic element and laser source may be configured to maintain eye-safe operation when viewed from a target area.

In some embodiments, changes in the incident angle between the optical signal and the diffractive optic element may cause a proportional change in the spacing between the elements of the structured light pattern. By adjusting the incident angle between optical signal and the diffractive optic element, the spacing between the elements of the structured light pattern may be expanded or contracted accordingly.

In step 320, an image is projected onto a target area. The strength of the light or the structured light pattern that is used may be based on a number of factors, including environmental factors such as weather or light conditions, the distance to a target area from diffractive optic element, and the structural and geographic features of the target area. For example, if the light source projecting the light is determined to be far away from target area, the light may be projected at a higher power. If closer, the light may be projected at a lower power. Other factors may include non-environmental factors, such as the characteristics of an electronic visual system.

In some embodiments, the power at which the light is projected may be adjusted manually and, in some cases, it may be adjusted automatically based on detected environmental factors. For example, the environmental factors may be detected by a detector within the light source itself, in another part of the system 100, or from an external source. In some embodiments, for example, the light source may be adjusted remotely, such as by a wireless signal transmitted from a location other than where the light source is.

In certain embodiments, a particular structured light pattern may be better suited for the geographic or structural elements of a particular target area. For example, if the target area is a narrow corridor in between two structures or within a single structure, a diffractive optic element may be chosen that produces a dense structured light pattern, such as multiple parallel lines, a dot array, or concentric circles. Under these circumstances, the area of denied visual access may be smaller. Thus, using a dense structured light pattern may provide more effective distribution of the light energy across the area of denied visual access. Alternatively, a less dense pattern may be chosen in certain situations and under certain conditions. For example, in a large area of denied visual access, the structured light pattern may be more disperse to effectively distribute the light energy across the larger area.

Consistent with some embodiments, patterns projected onto any portion of the target area are configured to be eye-safe when viewed from the target area consistent with Federal Aviation Administration (FAA), Occupational Safety and Health Administration (OSHA) or other standards that may be applicable to the area of implementation.

In step 330, the image is moved throughout the target area. The image may be moved by, for example, steering optical signal 130 to a new pointing position. In some embodiments, steering optical signal 130 may include using optical beam steering components between the output of light source 110 and diffractive optic element 140 to adjust the x and y positions of optical signal 130 without moving light source 110. That is, light source 110 may be stationary, while optical signal 130 may be steered to a new pointing position using optical beam steering techniques. In other embodiments, similar optical beam steering techniques and components may be used to adjust the pointing position by steering the structured light pattern as it leaves diffractive optic element 140. In this case, optical beam steering components may be coupled to receive the output of diffractive optic element.

In some embodiments, moving the image throughout target area 160 may include scanning the small area between the replicated pattern elements. For example, a projected structured light pattern 200 may be an array of lines with angular spacing of 1 degree between lines. Thus, by sweeping or steering the optical signal through 1 degree the projected pattern 200 would sweep through the 1 degree and illuminate all of the space between the lines in their initial stationary position. Redirection or scanning of optical signal 130 may be accomplished in any manner necessary to obtain the speed and resolution desired for a particular design application. In some embodiments, if diffractive optic element 140 is remotely located from light source 110 it may need to be adjusted to keep optical signal 130 within the aperture of diffractive optical element 140.

In some embodiments, the pointing position may be changed by adjusting the position of the light source relative to a fixed diffractive optic element. Changes to the position of the light source may be made in a controlled or pre-determined manner, in a random or pseudo random manner, or using a combination of both methods. For example, as shown in FIG. 1, light source 110 may be moved in multiple dimensions using positioning unit 120, causing a corresponding change to the pointing position of optical signal 130 coupled to diffractive optic element 140. Here, positioning unit 120 may be moved based on computer control, operator control, remote control, or a combination thereof. Further, the manner in which light source 110 is moved may be based on several factors, such as pattern spacing of the projected image, structural and geographic characteristics of the target area, environmental factors, or the type and/or severity of the threat. In some embodiments, the pre-determined or controlled movement may occur in some type of pattern, such as sweeping from one direction to another, in a circular motion, or in another suitable pattern. For certain applications, image 200 may be moved quickly and for others image 200 may be moved more slowly. Image 200 may also be repeatedly moved and stopped in either a periodic or aperiodic fashion, such that image 200 is stationary for some period of time.

In other embodiments, changes to the position of the light source relative to a fixed diffractive optic element may be made in a random or pseudo random manner. For example, a light source may experience random motion resulting from external forces such as the motion of a vehicle upon which the system may be mounted. System 100 may also be carried by a person, either stationary or moving. In this manner, system 100 may move with the person or vehicle. The transferred motion changes the pointing position of optical signal 130 coupled to diffractive optic element 140 by moving the position of light source 110, and thereby moving the output optical signal 130. The resulting induced random scan pattern causes image 200 to move across and illuminate target area 160 in a like manner, sufficiently redistributing the received energy associated with the structured light pattern throughout target area 160. For example, in operation, the elements of the structured light pattern associated with image 200 may repeat every five degrees. Thus, a stationary image 200 may have spaces between the pattern elements that would be free from illumination, and thus not subject to denial of visual access when projected onto a target area. The random movement of light source 110 as described above, would be designed to slightly exceed the five degree variation. Accordingly, the induced random movement of light source 110 may create a scan pattern with sufficient variation to cover the space between the elements of the structured light pattern, and thereby illuminate the entire target area.

In some embodiments, both light source 110 and diffractive optic element 140 are coupled together and may be moved in a random pattern in response to external forces as previously described. In other embodiments light source 110 and diffractive optic element 140 may be moved in a pre-determined or controlled manner using positioning unit 120 and optical mount 150 as previously described. Additionally or alternatively, one of light source 110 or diffractive optic element 140 may be moved in a random manner while the other component is moved in a pre-determined or controlled manner.

Returning to step 330, adjustments to the pointing angle may be configured to control the rate of motion and dwell time of the corresponding image projected onto target area 160. In some embodiments, the dwell time and the rate of motion may be determined based on the size of target area 160. The dwell time determines the duration of time that the image remains stationary within a portion of target area 160. The dwell time may be configured to cause image 200 to remain stationary long enough to create an ocular aversion response in the human eye without causing permanent injury to the eye. Alternatively, the dwell time may be configured to cause image 200 to remain stationary long enough to disrupt a biological or electronic visual system, sensor, or detector. In some cases, the disruption may be configured to affect principles of operation of the sensor. For example, the dwell time may be configured to disrupt the frame capture operation of a sensor associated with an electronic visual system. The rate of motion determines the sweep rate of the image across target area 160. In other words, the sweep rate defines how often the image reappears at a fixed location. The sweep rate may be configured to continually place the image at each location within target area 160 at a rate that prevents an observer in target area 160 from focusing on the object to be protected.

In other embodiments, when the light source is a pulsed laser, the pulse rate of the laser may also be a factor in determining the rate of motion and dwell time. To provide complete coverage of the target area, the pulse rate of the laser may be coordinated with the movement of the spots within structured light pattern that is the image. For example, if the spots comprising the structured light pattern move half of the original spot spacing for each laser pulse, pattern coverage remains sufficient. However, if spots move one and one-half of the original spot spacing for each laser pulse, blind spots may be created in the pattern.

By moving the image across a target area, an observer attempting to view the object to be protected from the target area will experience repeated ocular aversion responses. Ocular aversions may include, blinking, watery eyes, or pupil shrinkage. The degree of ocular aversion experienced is based, at least in part, on the broadcast intensity, sweep rate, and the dwell time of the moving image. For increased effectiveness, the sweep rate and dwell time provide repeated illumination of all locations within the target area sufficient to cause and/or recreate the aversion response. Similarly electronic visual systems may be disrupted by creating harmonic interference or overloading the system with excessive illumination.

In certain embodiments, the image may be moved throughout a target area in a pattern designed to prevent the use of visual systems or detectors in the target area. For example, the image may be moved across target area 160 based on a determined sweep rate and dwell time on an area equal to or greater than the receiving system's integration time. The sweep rate and dwell time may be configured to repeatedly expose the sensor associated with the visual system or detector to an excessive amount of energy, rendering the system inoperable.

Figure 4:
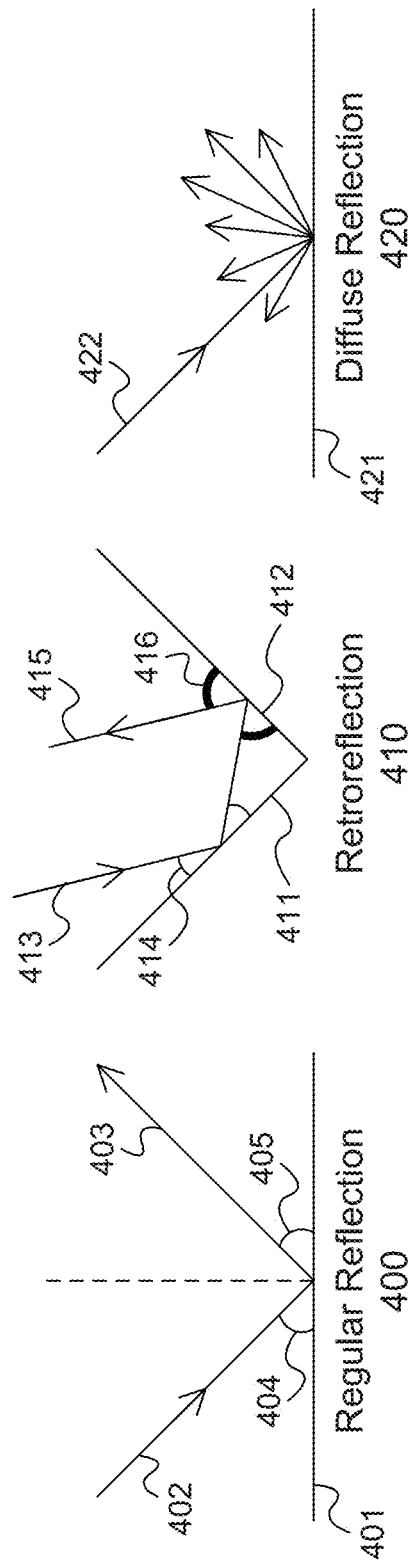
FIG. 4 illustrates the behavior of light interacting with various surface configurations.

FIG. 4 illustrates the behavior of light interacting with various surface configurations. Depending on the shape and reflective properties of a surface, an incident ray of light may reflect, retroreflect, or diffuse. For example, regular reflection 400 occurs when an incident beam of light 402 hits a reflective surface 401, such as a mirror, and reflects. In such a case, the angle of incidence 404 will equal the angle of reflection 405. 410 shows a simple two-dimensional case of so-called "corner retroreflection." Two mirrors 411 and 412 set at a right angle reflect the incident beam of light 413, directing the retroreflected beam 415 back in the direction of the source of the incident beam of light 413. 420 shows light diffusion, in which an incident beam of light 422 hits a nonreflective surface 421 such as a sheet of paper and scatters in many directions.

Figure 5:
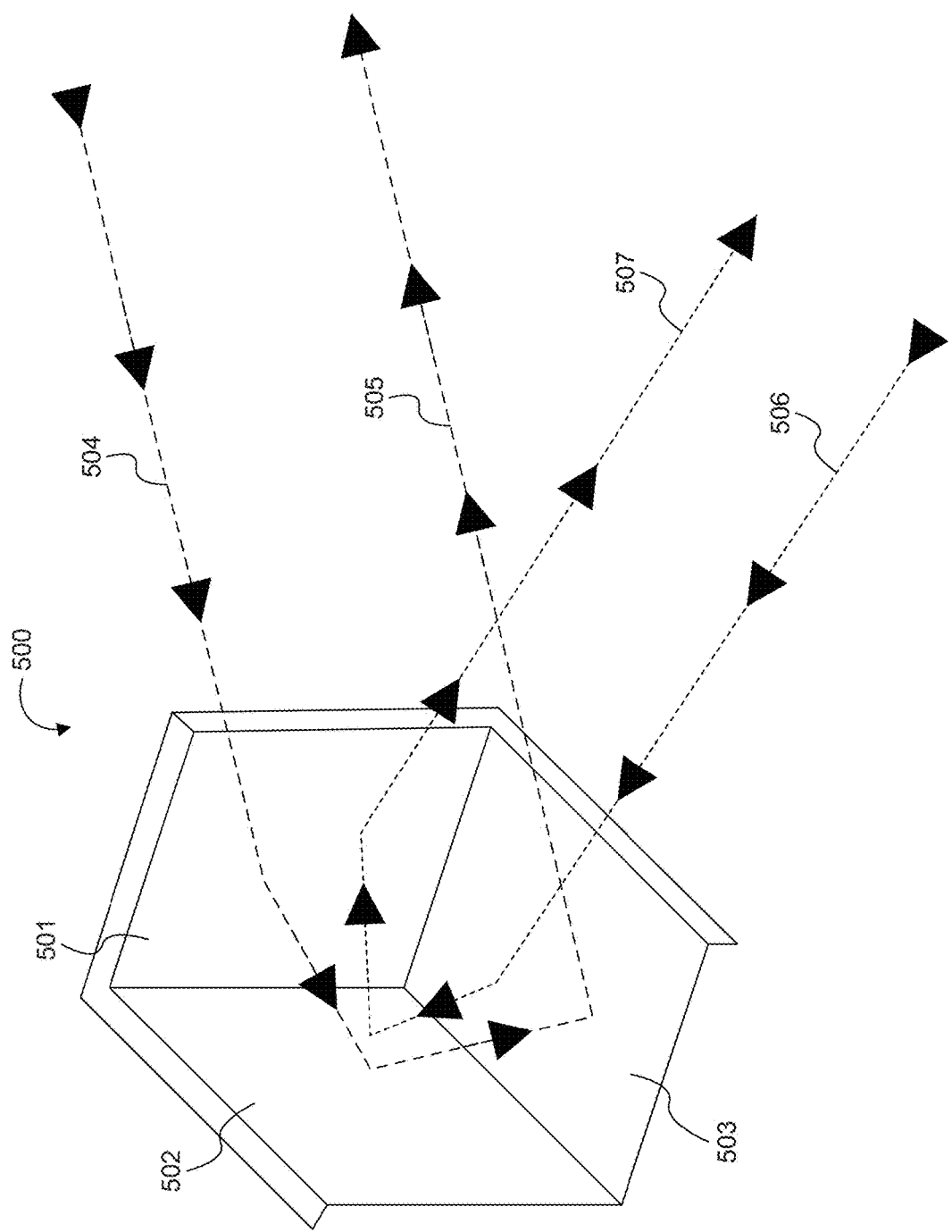
FIG. 5 illustrates the behavior of light in a corner retroreflector.

FIG. 5 illustrates the behavior of light in a corner retroreflector. FIG. 5 shows a three-dimensional corner reflector 500 similar to what would be found in a traffic sign or bicycle reflector. Corner reflector 500 has three mirror surfaces 501, 502, and 503 set at right angles to each other like the corner of a cube. It will reflect incident light beams 504 and 506 back towards their source via reflected beams 505 and 507, respectively.

Figure 6:
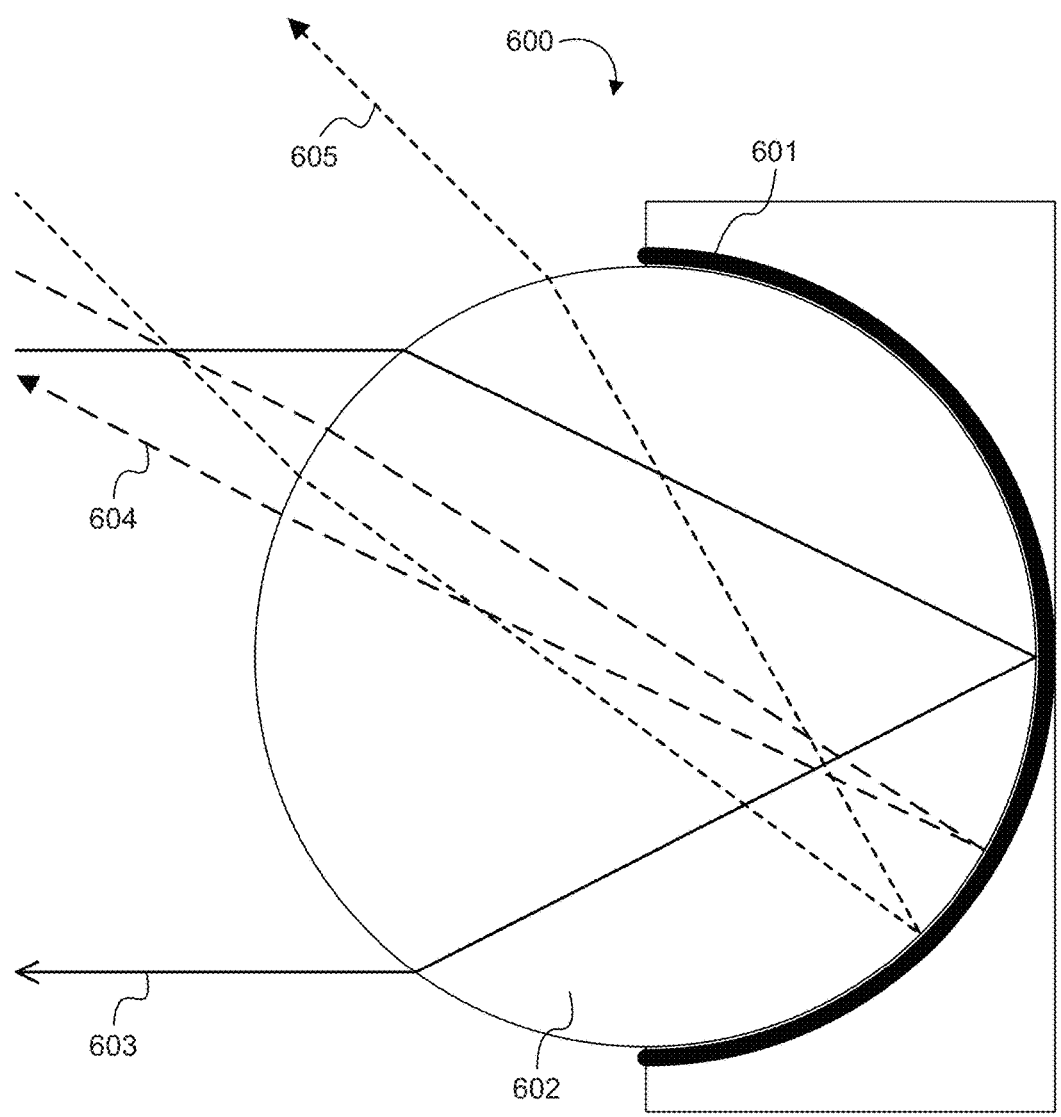
FIG. 6 illustrates the behavior of light in a spherical retroreflector.

Retroreflectors can take other forms in addition to the two- and three-dimensional corner reflectors described above. FIG. 6 illustrates the behavior of light in a spherical retroreflector 600. Spherical retroreflector 600 has a reflective surface 601, e.g., a mirror, and a transparent sphere 602. Reflective surface 601 may be fully reflective, partially reflective, or selectively reflective. A fully reflective surface may be created by optical coatings or a difference in refractive index. These same factors may create a partially or selectively reflective surface. Regardless of the implementation of the particular retroreflector, incident beams of light 603, 604, and 605 will be reflected back towards the direction of their source. Spherical retroreflectors are commonly called "cat's-eye" retroreflectors due to the tendency of animal eyes to act as retroreflectors.

A retro reflection is the return of light after being reflected from an optic element such as a lens, lens coating, mirror, sensor, optical filter or biology of a living eyeball. The cornea and or retina of a human or animal can reflect light. The measurable spectral qualities of the returned light can characterize the kind of sensor and can be used to adjust the dot projector parameters as well as the location or multiple locations of sensors or eyeballs. For example, a sniper's eye will reflect light and reflect a relative high amount of red in the return light. This is commonly known as "red eye" in flash photographs. Knowing that a human eye is in the area of concern and being able to identify the location of the eye can be important. Another application may be in the identification of animal locations such as birds, cats or other animals of interest in a forest. This could assist with population estimates of species that are difficult to locate in rugged terrain.

The qualities of the retro reflection can assist with the characterization of nonbiological electronic sensors as well. The characterization or determination of the sensor type or whether the optical element is a living or machine sensor can be used to determine the best spectral frequency of the projected dots of light and or the required pulse width or intensity to defeat a sensor system and/or quantify the threat. For example, the return from a sniper looking through an optical rifle scope will be different than a shooter with only a pistol, which will usually not have an optical scope.

In the instance of video cameras or thermal sensors, the reflected light can be measured. Different lens coatings and optical coatings on sensors that are specific to the character type of the sensor will reflect light with unique absorbance and reflectance intensities in specific spectral bands. These can be used to determine if a camera is thermal, has infrared (IR) filters or not.

For example, if it is determined that a sensor is a video camera with sensitivity to only visible light and it is not reflecting the anticipated light between 400 nm and 700 nm but it is returning IR above 700 nm, then the bands for the red, green, and blue channels can be selected for projection because the camera is a video camera most sensitive to visible bands, and the projection of such bands toward the camera will temporarily disrupt reception or permanently burn out the light sensitive device, depending on the desire of the operator of the projector. If it is determined that the camera is reflecting most of the visible light, but not reflecting IR bands above 700 nm, then the sensor can be characterized as IR and the projector can be adjusted to use IR light with wavelengths longer than 700 nm. In addition, many commercially available video cameras have frame rates corresponding to PAL and NTSC standards. Thus, projector pulse width and repetition can be adjusted for maximum disruption of cameras receiving video at, for example, 48-50 frames per second. The movement of the pattern can be adjusted to maximize the interference with the sensor. In the instance of a human being, the power can be adjusted to the maximum allowable safe exposure to laser light levels while still stimulating a blink or obscuration response by the sniper's eye and eyelid.

The location of the sensor can be determined by a sensor designed for this purpose. By determining the position of the moving dots at the time a return was detected, the location can be determined as multiple passes are made. For example, an imaging sensor such as a video camera would record the vertical and horizontal angles from the projector's position. These angles could then be plotted to an intercept with the geography/volume of denied access. The projector can also systematically project dots that have variable intensities, timing pulse patterns, and or spectral qualities to isolate the location by determining which dot is creating the detected return.

Figure 7:
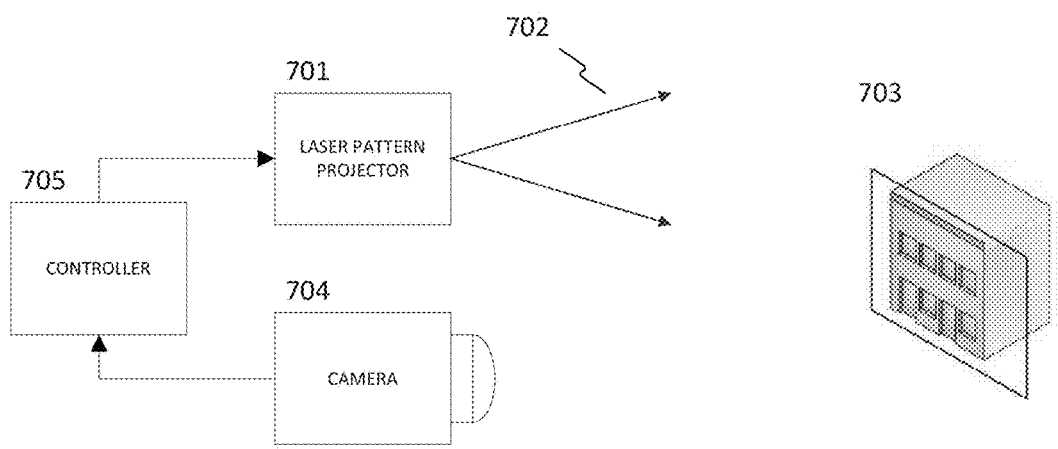
FIG. 7 shows an exemplary system for characterizing a sensor based on reflected and retroreflected light.

FIG. 7 shows an exemplary system for characterizing a sensor based on reflected and retroreflected light. Laser pattern projector 701, similar to the one described in system 100 and under the control of controller 705, projects a laser pattern 702 onto target area 703. Detection device 704 detects reflections and retroreflections returning from target area 703 and sends data related to both back to controller 705. Controller 705 analyzes the reflection and retroreflection data and characterizes the sensor. Controller 705 then adjusts its output to produce the desired effect on the sensors detected in target area 703.

Figure 8:
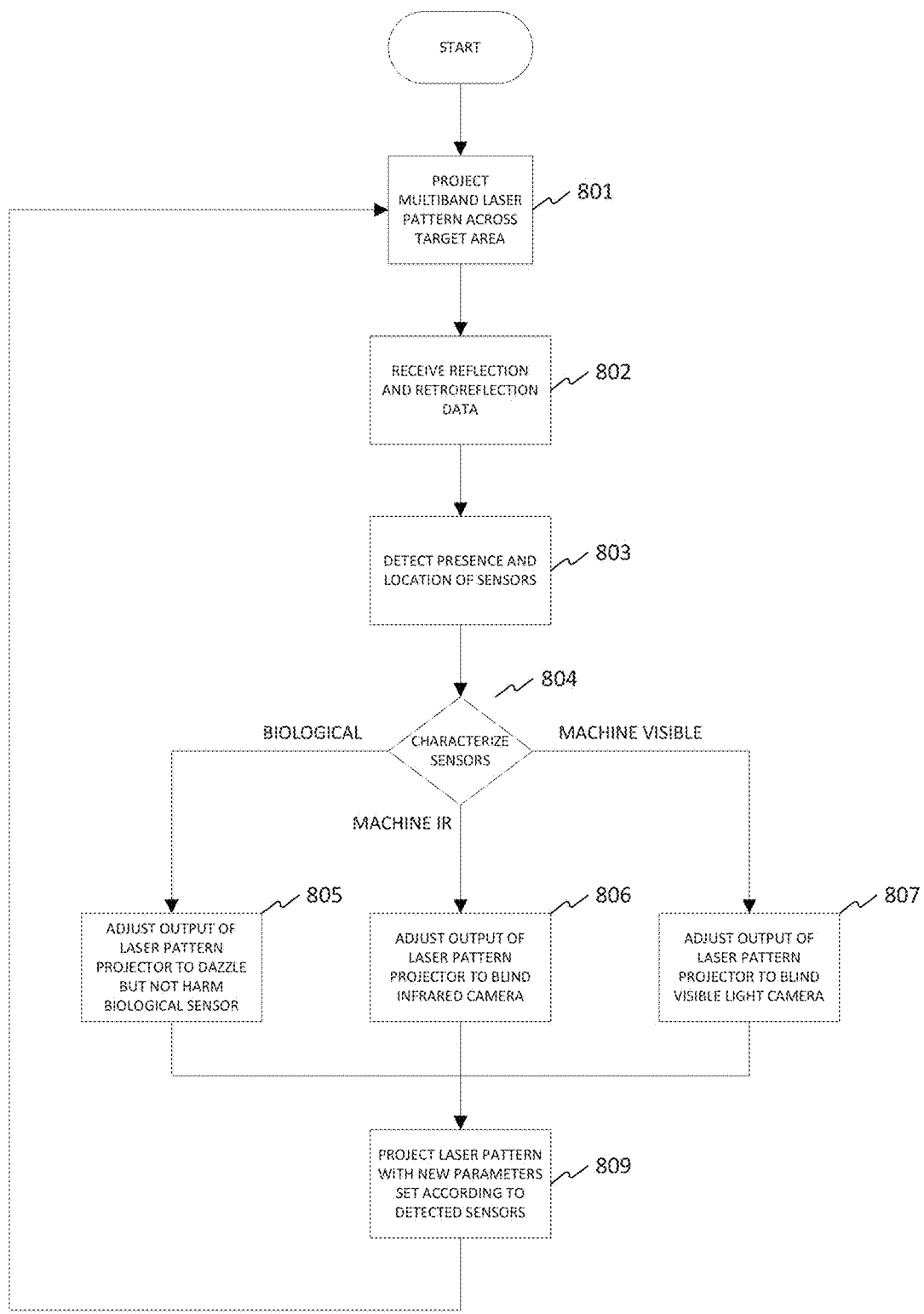
FIG. 8 shows a flowchart illustrating steps in an exemplary method for characterizing a sensor based on reflected and retroreflected light.

FIG. 8 shows a flowchart illustrating steps in an exemplary method for characterizing a sensor based on reflected and retroreflected light. In step 701, laser pattern projector system 100 projects a multiband laser pattern 702 across a target area 703. In step 802 detection device 704 receives light reflected and retroreflected from target area 703, and sends the data related to each to controller 705. In step 803, controller 705 processes the reflection and retroreflection data to determine the presence and location of any sensors detected in target area 703. In step 804 controller 705 further processes the reflection and retroreflection data to determine the type of sensor detected in target area 703. For example, the presence of retroreflected light concentrated mostly in the red spectrum of visible light may indicate a human biological sensor; i.e., the eye of human. More detailed characterization can be made for biological sensors. For example, while the retroreflection from a human eye is strongly red, the retroreflection from cats and other nocturnal or crepuscular animals may be more greenish or broadband. If a retroreflection is detected with a concentration in the infrared spectrum (wavelengths longer than 700 nm), then the sensor is likely a camera sensitive to light in the visible spectrum. In contrast, if a retroreflection is detected with a concentration in the visible light spectrum, but is dark in the infrared spectrum, the sensor is likely a camera sensitive to light in the infrared spectrum, such as a thermal imager or night-vision apparatus. In a further example, a rifle or spotting scope may display a different reflective and retroreflective character. For example, a time history of multiple overlapping reflections will reveal that the lenses in the scope will likely have different spectral content from the retro reflection of the eye behind the scope.

Once the type of sensor has been determined in step 804, the output of the projector can be adjusted to provide the desired amount of disruption or damage to the sensor detected. For example, if human eyes are detected, the projector output may be adjusted to "dazzle," or temporarily blind, the person (step 805). If a machine sensor, such as a camera, is detected, the wavelength of light and intensity can be adjusted based on the camera type, and on whether the operator wishes to temporarily obstruct the camera's view with a relatively low-intensity projection, or permanently burn out the light-sensitive device (step 806 or 807). Finally, in step 809, controller 705 makes the appropriate adjustment to the output of projector 701. For example the diffractive optic could be removed and a direct beam might be directed at the proper intensity and direction to the detected threat.

In various embodiments, one or more of the modules disclosed in this disclosure are implemented via one or more computer processors executing software programs for performing the functionality of the corresponding modules. In some embodiments, one or more of the disclosed modules are implemented via one or more hardware modules executing firmware for performing the functionality of the corresponding modules. In various embodiments, one or more of the disclosed modules include storage media for storing data used by the module, or software or firmware programs executed by the module. In various embodiments, one or more of the disclosed modules or disclosed storage media are internal or external to the disclosed systems. In some embodiments, one or more of the disclosed modules or storage media are implemented via a computing "cloud", to which the disclosed system connects via an internet and accordingly uses the external module or storage medium. In some embodiments, the disclosed storage media for storing information include non-transitory computer-readable media, such as a CD-ROM, computer storage, e.g., a hard disk, or a flash memory. Further, in various embodiments, one or more of the storage media are non-transitory computer-readable media store information or software programs executed by various modules or implementing various methods or flow charts disclosed herein.

The foregoing description of the invention, along with its associated embodiments, has been presented for purposes of illustration only. It is not exhaustive and does not limit the invention to the precise form disclosed. Those skilled in the art will appreciate from the foregoing description that modifications and variations are possible in light of the above teachings or may be acquired from practicing the invention. For example, the steps described need not be performed in the same sequence discussed or with the same degree of separation. Likewise various steps may be omitted, repeated, or combined, as necessary, to achieve the same or similar objectives. Similarly, the systems described need not necessarily include all parts described in the embodiments, and may also include other parts not described in the embodiments. Accordingly, the invention is not limited to the above-described embodiments, but instead is defined by the appended claims in light of their full scope of equivalents.

What is claimed is:

1. A method for denying visual access from a target area, the method comprising:
   generating a structured light pattern with a laser pattern projector that projects light including a plurality of wavelengths;
   projecting the structured light pattern onto the target area;
   receiving light returning from the target area, the received light comprising reflected and retroreflected light;
   detecting a presence of a sensor in the target area; and
   analyzing the received light to characterize the sensor, wherein the sensor is characterized as a biological sensor, a visible light camera, or an infrared camera based on spectral ratios of the received light.

2. The method of claim 1, further comprising determining a location of the sensor according to an azimuth and elevation of the received light.

3. The method of claim 1, further comprising adjusting a wavelength, pattern, movement, and/or intensity of the structured light pattern based on a character of the sensor.

4. A system for characterizing a sensor in a target area, the system comprising:
   one or more lasers and a diffractive optic element configured to project a structured light pattern including a plurality of wavelengths onto a target area, wherein projecting the structured light pattern onto the target area further comprises moving the structured light pattern to scan the target area between elements of the structured light pattern;
   a detection device configured to:
      receive light returning from the target area, the received light comprising reflected and retroreflected light, and
      generate data corresponding to the received light; and
   a controller configured to:
      receive the data;
      analyze the data to determine a presence of a sensor in the target area; and
      further analyze the data to characterize the sensor, wherein the sensor is characterized as a biological sensor, a visible light camera, or an infrared camera based on spectral ratios of the received light.

5. The system of claim 4, wherein the controller is further configured to locate the sensor according to an azimuth and elevation of the received light.

6. The system of claim 4, wherein the controller is further configured to adjust a wavelength, pattern, movement, and/or intensity of the structured light pattern based on a character of the sensor.

7. The method of claim 1, wherein projecting the structured light pattern onto the target area further comprises adjusting a spacing between elements of the structured light pattern and moving the structured light pattern to scan the target area between the elements of the structured light pattern.

* * * * *